US009161923B2

(12) United States Patent
Holden

(10) Patent No.: US 9,161,923 B2
(45) Date of Patent: Oct. 20, 2015

(54) COMPOSITION FOR PREVENTION AND TREATMENT OF CONTACT LENS PAPILLARY CONJUNCTIVITIS AND ALLERGIC EYE DISEASE

(75) Inventor: Brien Anthony Holden, Sydney (AU)

(73) Assignee: Brien Holden Vision Institute, Sydney, NSW (AU)

( * ) Notice: Subject to any disclaimer, the term of this patent is extended or adjusted under 35 U.S.C. 154(b) by 0 days.

(21) Appl. No.: 13/806,249

(22) PCT Filed: Jul. 1, 2011

(86) PCT No.: PCT/AU2011/000827
§ 371 (c)(1),
(2), (4) Date: Dec. 21, 2012

(87) PCT Pub. No.: WO2012/000055
PCT Pub. Date: Jan. 5, 2012

(65) Prior Publication Data
US 2013/0102679 A1 Apr. 25, 2013

(30) Foreign Application Priority Data
Jul. 2, 2010 (AU) ................................ 2010902954

(51) Int. Cl.
*A61K 31/164* (2006.01)
*A61K 9/06* (2006.01)
*A61K 9/08* (2006.01)
*A61K 9/10* (2006.01)
*A61K 9/00* (2006.01)

(52) U.S. Cl.
CPC ............. *A61K 31/164* (2013.01); *A61K 9/0048* (2013.01); *A61K 9/08* (2013.01)

(58) Field of Classification Search
None
See application file for complete search history.

(56) References Cited

U.S. PATENT DOCUMENTS

| 2005/0164979 | A1* | 7/2005 | Gross et al. | .................. 514/54 |
| 2005/0220742 | A1 | 10/2005 | Breen | |
| 2007/0027048 | A1* | 2/2007 | Schwind et al. | .............. 510/112 |
| 2007/0104744 | A1 | 5/2007 | Smith | |
| 2007/0243275 | A1 | 10/2007 | Gilbard | |
| 2010/0087550 | A1 | 4/2010 | Marlowe et al. | |

FOREIGN PATENT DOCUMENTS

| CA | 2468771 | 6/2003 |
| EP | 2251003 | 11/2010 |
| WO | 20021060495 A1 | 8/2002 |
| WO | 2009/094466 A2 | 7/2009 |
| WO | 2010056113 | 5/2010 |
| WO | 2010127227 | 11/2010 |

OTHER PUBLICATIONS

Sindt et al., "Contact Lens Strategies for the Patient with Dry Eye", Oct. 2007, The Ocular Surface, vol. 5, No. 4, pp. 294-307.*
The International-Type Search Reported of Australian National Application No. 2010902954 dated Jul. 2, 2010.
Smolle, Michaela et al., "Clear hydro-gel, compared to ointment, provides improved eye comfort after brief surgery" Canadian Journal of Anaesthesia (2004), vol. 51(2), pp. 126-129.
Raczynska, K. et al., "Clinical evaluation of drops and gel with provitamin B5 in postoperative treatment of cornea and conjunctiva wounds" Klinika oczna (2003), vol. 105(3-4), pp. 175-178.
Patient Use Information, "Gebrauchsinformation Pan-Ophtal®Augentropfen, Wirkstoff: Dexpanthenol, Dr. Winzer" Jun. 2005, Dr. Winzer Pharma GMBH, 13581 Berlin.
Pan-Ophtal: "Gebrauchs information: Information fur den Anwender: Pan-Ophtal Gel" XP055088010 (Jun. 1, 2006), pp. 1-2, Retrieved from Internet: URL:https://www.aliva.de/images/ecommere/02/00/02003563_2006-06_de_o.pdf [retrieved on Nov. 13, 2013].
Documed AG: "cornpendium.ch—Bapanthen Augentropfen", XP055088074, (Sep. 1, 2009), Retrieved from the Internet: URL:http://compendium.ch/mpub/pnr/1163361/html/de [retrieved on Nov. 13, 2013].
Extended European Search Report of PCT/AU2011000827 dated Nov. 21, 2013.
Weissman, B.A. (2013) "Giant Papillary Conjunctivitis" available online at http://emedicine.medscape.com/article/1191641-overview.

* cited by examiner

*Primary Examiner* — Michael B Pallay
(74) *Attorney, Agent, or Firm* — Jones Day

(57) ABSTRACT

The invention provides a use of panthenol or dexpanthenol in the prevention and/or treatment of contact lens papillary conjunctivitis in a subject. A contact lens care solution containing 0.001 to 10% by dry weight dexpanthenol is also provided.

31 Claims, No Drawings

COMPOSITION FOR PREVENTION AND TREATMENT OF CONTACT LENS PAPILLARY CONJUNCTIVITIS AND ALLERGIC EYE DISEASE

This application is a U.S. national phase of International Application No. PCT/AU2011/000827, filed Jul. 1, 2011, the disclosure of which is hereby incorporated by reference in its entirety.

FIELD OF THE INVENTION

The present invention relates to pharmaceutical eye compositions comprising panthenol or dexpanthenol and their use for the prevention and/or treatment of contact lens papillary conjunctivitis, mechanical trauma and friction-induced eye disease and allergic eye disease. In a preferred embodiment, the eye disease is contact lens papillary conjunctivitis.

BACKGROUND OF THE INVENTION

Contact lens papillary conjunctivitis, also known as giant papillary conjunctivitis, occurs in contact lens wearers and is one of the major reasons that contact lens wearers discontinue lens wear. The signs of the condition can range from mild redness of the upper tarsus with few papillae to severe redness with large cobblestone papillae. The condition has been observed with all types of contact lenses i.e. hard or polymethyl methacrylate (PMMA) lens wear, rigid gas permeable lenses, soft lenses and also silicone hydrogel contact lenses. The condition results in acute patient discomfort, intolerance to contact lens wear, itching, mucus discharge, excessive movement of the lens on the eye and deposits on the lens. Often lens wearers are required to reduce the wearing time of lenses to reduce the frequency of symptoms but left unmanaged the condition ultimately leads to drop outs from lens wear. The incidence of the condition is reported to range from 1.0 to 18.0% depending on the type (soft, rigid gas permeable or silicone hydrogel), mode (daily wear or extended wear) and frequency of replacement of lens wear (daily replacement or weekly or monthly).

Contact lens papillary conjunctivitis is considered to be caused by either or both mechanical irritation or inflammatory reaction. The mechanical aetiology is assumed to derive from a combination of a lack of surface lubrication, friction and surface irregularities of the contact lens. Deposits on the lenses can also cause mechanical irritation. The inflammatory reaction or allergic aetiology is usually related to deposits that build up on the lenses, for example the lens wearer's own lipids, proteins, preservatives in the contact lens solutions that build up on the lens, environmental allergens that build up on the lens, and possibly reaction to the lens material. In this condition papillae form on the upper tarsal conjunctiva of the upper eyelid, which cause discomfort due to the sensitive nature of the tissue.

Contact lens papillary conjunctivitis may also be associated with allergic eye disease which encompasses other notable conditions such as allergic conjunctivitis and vernal conjunctivitis. Allergic conjunctivitis is widely prevalent with estimates suggesting that anywhere from 9 to 18% of the population may be affected. The condition is characterised by itching of the eye and subjects may also complain of tearing, redness and burning. The symptoms could be seasonal or constant in nature. Ocular examination is characterised by redness of the conjunctiva and in some instances presence of small papillae on the upper tarsal conjunctiva (raised polygonal structures on the inside of the upper lid giving the tissue a roughened appearance). In the more serious variants of allergic eye disease, vernal conjunctivitis presents as a more severe, chronic condition primarily affecting children and young adults. Symptoms include severe itching, tearing, foreign body sensation, mucus discharge and photophobia. The condition is characterised by redness of the conjunctiva and giant, cobble stone papillary reaction of the upper tarsal conjunctiva. Variants of the condition are characterised by limbal conjunctival involvement and also corneal erosions.

People who get allergic conjunctivitis or vernal conjunctivitis or contact lens papillary conjunctivitis once often become more susceptible to the condition in the future. The onset of these forms of conjunctivitis may be triggered by the wearing of contact lenses, which leads to a strong incentive to stop the use of contact lenses. Although the occurrence of subsequent instances of contact lens papillary conjunctivitis can be reduced by using daily lenses, this is not an ideal solution. Avoiding an initial episode would therefore be desirable.

Existing methods of treatment of both contact lens papillary conjunctivitis and allergic eye disease using eye drops, for example the application of steroids, are hampered by the effect of the eye to quickly drain off tears. There remains therefore a significant challenge in treating the above conditions safely, conveniently and cost-effectively.

Dexpanthenol is known as a B vitamin having a preservative effect but not as a treatment for contact lens papillary conjunctivitis and allergic eye disease.

US 2005/0164979 describes use of a composition containing a combination of panthenol or dexpanthenol and hyaluronic acid and/or hyaluronate for the treatment of various ophthalmological and rhinological malfunctions, including allergic rhinoconjunctivitis, atopic keratoconjunctivitis, allergic keratoconjunctavitis, gigantopapillary conjunctivitis, conjunctivitis vernalis, episcleritis such as for example episcleritis periodica, episcleritis partilis fugax, scleritis, tendonitis, Sjogren syndrome or hybrid forms thereof. It was found that the application of panthenol in combination with hyaluronic acid leads to rapid epithelialisation and therefore wound healing. Hyaluronic acid is described as playing a dual role in inflammation: it is both pro- and anti-inflammatory. It is pro-inflammatory in the initial phases promoting wound healing.

US 2007/0104744 describes a contact lens solution comprising a preservative enhancer (0.00001 to 10%) chosen from various B family vitamins together with the preservative to be enhanced, optionally with buffers and various other excipients. Dexpanthenol is one of the B vitamins described as enhancing the effect of the preservative in the solution.

WO 2010/056113 describes a combination of carnosine and dexpanthenol in a contact lens care solution. The solution is described as useful in preventing or treating corneal staining.

US 2007/0027048 describes a solution containing dexpanthenol for cleansing contact lenses and stabilising the lachrymal film.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

The subject invention comprises the surprising effect of dexpanthenol (an alcohol form of the dextrorotatory isomer of pantothenic acid). The inventors have surprisingly found that when dexpanthenol (an alcohol form of the dextrorotatory isomer of pantothenic acid) is included in preparations applied to the eye, it reduces the occurrence of either or both of papillae on the upper tarsal conjunctiva and signs of redness of the eye. In particular, the inventors have found that a contact lens care solution containing dexpanthenol in which the contact lens is soaked prior to being fitted to the eye of the subject reduces the occurrence of these symptoms.

Accordingly, the present invention relates to the use of panthenol or dexpanthenol in the prevention and/or treatment of contact lens papillary conjunctivitis in a subject. The invention also relates to the use of panthenol or dexpanthenol in the prevention and/or treatment of mechanical trauma and friction-induced eye disease in a subject. The invention also relates to the prevention and/or treatment of allergic eye disease in a subject. In one embodiment, the allergic eye disease is allergic conjunctivitis or vernal conjunctivitis. A therapeutically effective amount of dexpanthenol is used.

The invention is generally described by reference to dexpanthenol but panthenol (ie the racemic mixture) and/or (dex) panthenoic acid is also suitable for use in the present invention.

Preferably the disease to be treated or prevented is caused by the wearing of the opthalmic device, such as a contact lens.

The use of dexpanthenol also provides an alternative to use of long term therapy with non-steroidal anti-inflammatory agents and corticosteroids commonly used in the treatment of allergic eye disease which are associated with undesirable side effects. Existing methods of treatment involve the use of eye drops which are quickly drained away by tears which leads to inconsistent results in respect of treatment of the eye disease. An advantage of dexpanthenol in the present invention is that it can be administered in higher quantities than the more potent actives, without any deleterious effect. This means that more dexpanthenol can be applied to the eye and therefore more dexpanthenol is present on the eye to treat the disease, before the dexpanthenol is washed away. Another advantage is that dexpanthenol can be used in a contact care solution or directly applied to the contact lens so as to be administered to the eye via the contact lens when fitted. This means that the likelihood of dexpanthenol being drained away by tears that may occur via other modes of administration is reduced. Dexpanthenol may then be slowly absorbed into to relevant area, particularly the upper tarsal conjunctiva of the upper eyelid whilst fitted to the eye.

In preferred embodiments, the invention is directed to a subject first assessed as being in need of treatment for contact lens papillary conjunctivitis. In another embodiment the subject is first assessed as being in need of treatment for mechanical trauma and friction-induced eye disease and/or or allergic eye disease such as allergic conjunctivitis or vernal conjunctivitis. Alternatively, the subject is first assessed as being at risk of developing any of these conditions (e.g. due to initial or resumed wearing of contact lenses) or to be at particular risk (e.g. from complications or consequence of developing the condition) if one of these conditions developed, such that preventing or inhibiting the development of these conditions was considered necessary. In this respect, the low risk of administering dexpanthenol, soluble in water, is relevant to the safe implementation of the method of the invention.

The present invention also relates to the use of a therapeutically effective amount of dexpanthenol in the prevention and/or treatment in a subject of one or more of contact lens papillary conjunctivitis, mechanical trauma and friction-induced eye disease, and allergic eye disease, in particular contact lens papillary conjunctivitis. In other words, the invention includes both reducing the risk of contracting these conditions by inhibiting or preventing their initial development, as well as in another embodiment treating those conditions once diagnosed.

In another embodiment, dexpanthenol is administered in the form of a pharmaceutical composition. Accordingly, the present invention provides a pharmaceutical composition comprising panthenol or dexpanthenol. In one form of the invention, the only active component in the composition is panthenol or dexpanthenol, preferably dexpanthenol. The pharmaceutical composition is preferably in a form suitable for administration to the eye such as an ointment, gel, spray, eye drop or by release from a contact lens that is fitted to the eye. In the case of a spray, the patient would turn their eyelid inside-out to allow application of the spray. The concentration of dexpanthenol in the composition is from 0.001 to 10% by dry weight. In specific embodiments it is between 0.01 to 5% and 0.1 to 1% by dry weight. Preferably it is about 2% by dry weight. In another embodiment, the composition is an aqueous composition, which is isotonic.

In another embodiment, there is provided a contact lens care solution containing panthenol or dexpanthenol. In one form of the invention, the only active component in the care solution is dexpanthenol. According to this embodiment the care solution is formulated so as to permit the lens to absorb and/or adsorb dexpanthenol from the solution and then release it into the eye during wear. The concentration of dexpanthenol in the care solution may be from 0.001 to 10% by dry weight. In specific embodiments it is between 0.01 to 5% and 0.1 to 1% by dry weight. Preferably it is about 2% by dry weight. In another embodiment, the solution is an aqueous solution, which is isotonic.

In other embodiments, the composition or care solutions described above consist essentially of one active component for prevention and/or treatment of one or more of contact lens papillary conjunctivitis, mechanical trauma and friction-induced eye disease, and allergic eye disease, wherein the active is dexpanthenol. In this specification "consists essentially of" means that the composition or contact lens care solution according to the invention contains only one active pharmaceutical ingredient but may optionally include other non-active components such as salts and buffers in aqueous solution.

In one embodiment, the composition or care solutions described above may further include a preservative. Suitable preservatives include benzalkonium chloride, Chlorhexidine, polymyxin B sulphate, sorbic acid and Purite®. Such preservatives would not be considered by a person skilled in the art as an active component of the composition or care solution suitable for the prevention or treatment of one or more of contact lens papillary conjunctivitis, mechanical trauma and friction-induced eye disease, and allergic eye disease. In an alternative embodiment the composition or care solutions described above do not include a preservative, ie, are preservative-free.

Preferably, the pharmaceutical composition according to the present invention is formulated for topical administration. Preferably, the composition of the present invention is in a form suitable for administration to the eye e.g. an eye drop, a spray or by release from a soft contact lens. In the case of the contact lens the active is either coated on the surface of the lens or absorbed into the matrix of material of the lens.

The present invention also relates to the use of a composition or contact lens care solution containing dexpanthenol in the prevention and/or treatment in a subject of one or more of contact lens papillary conjunctivitis, mechanical trauma and friction-induced eye disease and allergic eye disease, preferably contact lens papillary conjunctivitis.

In a further embodiment, the composition or care solution consists of dexpanthenol, water and optionally salt and/or buffer, wherein the composition is isotonic.

The present invention also relates to a method of preventing and/or treating contact lens papillary conjunctivitis, mechanical trauma and friction-induced eye disease or allergic eye disease, preferably contact lens papillary conjunctivitis, comprising administration of a therapeutically effective amount of dexpanthenol, optionally in a pharmaceutical composition or contact lens care solution as described above. The present invention also relates to the use of a therapeutically effective amount of dexpanthenol for the prevention and/or treatment of one or more of contact lens papillary conjunctivitis, mechanical trauma and friction-induced eye disease or allergic eye disease, preferably contact lens papillary conjunctivitis.

The present invention also provides a pharmaceutical composition or contact lens care solution for use in the prevention and/or treatment of one or more of contact lens papillary conjunctivitis, mechanical trauma and friction-induced eye disease or allergic eye disease, preferably contact lens papillary conjunctivitis, as described above in any of the embodiments of the invention.

The present invention also relates to the use of a therapeutically effective amount of dexpanthenol for the manufacture of a medicament for the prevention and/or treatment of one or more of contact lens papillary conjunctivitis, mechanical trauma and friction-induced eye disease or allergic eye disease, preferably contact lens papillary conjunctivitis.

The present invention also relates to dexpanthenol when used in a method of preventing and/or treating one or more of contact lens papillary conjunctivitis mechanical trauma and friction-induced eye disease or allergic eye disease, preferably contact lens papillary conjunctivitis.

The present invention also relates to a composition having an active ingredient for use in the prevention and/or treatment of one or more of contact lens papillary conjunctivitis, mechanical trauma and friction-induced eye disease or allergic eye disease, preferably contact lens papillary conjunctivitis, wherein the active ingredient is dexpanthenol.

The present invention also relates to the use of an ophthalmic device containing dexpanthenol in the prevention and/or treatment of one or more of contact lens papillary conjunctivitis, mechanical trauma and friction-induced eye disease or allergic eye disease, preferably contact lens papillary conjunctivitis, such as described above. Such an ophthalmic device may be an ocular insert intended for application between the eyelids and sclera from which dexpanthenol may be released into the eye, such as a contact lens.

The present invention also relates to a method of making an ophthalmic device for the prevention and/or treatment of one or more of contact lens papillary conjunctivitis, mechanical trauma and friction-induced eye disease or allergic eye disease, preferably contact lens papillary conjunctivitis, by a therapeutically effective amount of dexpanthenol, comprising the step of contacting an ophthalmic device with a solution comprising dexpanthenol and then applying the device to the eye. In one embodiment the ophthalmic device is a contact lens. Preferably, the contact lens is a soft contact lens. The lens may be prepared by soaking the lens in a care solution containing dexpanthenol. Typically, the lens is soaked in the solution for 15 mins to 3 hours, preferably for 1 hour. In some instances the contact lens may be stored in the contact lens care solution overnight. The lens may also be prepared by a) dexpanthenol incorporated liposomes that are attached to the lens surface and b) a care solution formulation of dexpanthenol being incorporated into the packaging solution in the case of disposable lenses (e.g. daily lenses). The dexpanthenol is desirably present in the solution in an amount ranging from 0.01 to 10% weight by volume. In specific embodiments it is between 0.01 to 5% and 0.1 to 1% weight by volume. Preferably it is about 2% weight by volume.

Embodiments of the invention in which the dexpanthenol is released from an ophthalmic device are advantageous in that the device (such as a contact lens) maintains the solution in contact with the eye-lid every time the wearer blinks, as opposed to eye drops or a spray which may be relatively quickly drained off the eye by the normal tear action. Without being bound by any particular mode of action it is believed that dexpanthenol is absorbed into the matrix of the device or coated onto the surface of the device when soaked in the care solution. Dexpanthenol can then be absorbed from the contact lens into the treatment area (ie, upper tarsal conjunctiva of the upper eyelid).

The present invention also relates to an ophthalmic device comprising dexpanthenol. Preferably the ophthalmic device is a contact lens. In this embodiment the dexpanthenol is absorbed into the matrix of the device or coats the surface of the device.

The present invention also provides a method for coating an ophthalmic device with dexpanthenol including the step of contacting the device with a composition including dexpanthenol for a time sufficient to coat the device. Preferably the device is a contact lens. The present invention also provides a method for producing an opthalmic device comprising dexpanthenol including the step of contacting the device with a composition including dexpanthenol for a time sufficient for dexpanthanol to be absorbed into the matrix of the device. Preferably the device is a contact lens. The present invention also provides an ophthalmic device coated with dexpanthenol or an ophthalmic device comprising dexpanthenol. According to these aspects of the invention the ophthalmic device is suitable for prevention and/or treatment of one or more of contact lens papillary conjunctivitis, mechanical trauma and friction-induced eye disease or allergic eye disease, preferably contact lens papillary conjunctivitis.

The present invention also provides a method of prevention and/or treatment of one or more of contact lens papillary conjunctivitis, mechanical trauma and friction-induced eye disease or allergic eye disease, preferably contact lens papillary conjunctivitis by treating an opthalmic device with a composition including dexpanthenol. The present invention also provides a method of prevention and/or treatment of one or more of contact lens papillary conjunctivitis, mechanical trauma and friction-induced eye disease or allergic eye disease, preferably contact lens papillary conjunctivitis, caused by the wearing of contact lenses by treating the contact lens with a composition including dexpanthenol or a contact lens care solution.

In forms of the invention described by any of these embodiments, dexpanthenol is essentially the only active ingredient of the composition or care solution. In one embodiment, the composition or care solution is preferably without or free of one or more pro-inflammatory, anti-inflammatory, wound healing, antibacterial (including bacteriocidal and bacteriostatic), antifungal, antiviral, antioxidant, antibiofilm and preservative-enhancing agents, and/or one or more preservatives. In one embodiment, the composition or care solution has no hyaluronic acid and/or hyaluronate. In another embodiment, the composition or care solution also has no peptide component, in particular no carnosine. In another embodiment, the composition or care solution has no hexamidine diisethionate, polyhexanide hydrochloride, chlorhexidine digluconate or methylsulphonylmethane. In a further embodiment, the composition or care solution has no natural oils, or compounds found in natural oils (e.g. linalool oil, α-terpineol oil, hinokitiol). In another embodiment, the composition or care solution has no alcohol (e.g. a diol, such as a glycol). In a further embodiment, the composition or care solution has no vitamin(s) (e.g. vitamins A and/or E). Preferably, the composition excludes or is substantially free of any preservative, hyaluronic acid and/or hyaluronate and any peptide component, in particular no carnosine.

In another embodiment there is provided a kit for use in a method of the invention mentioned above, the kit including:
   a container holding dexpanthenol or pharmaceutical composition or contact lens care solution of the invention; and
   a label or package insert with instructions for use.

Optionally, the kit includes a vessel for containing a contact lens soaking in the composition or contact lens care solution and/or a device for dispensing eye-drops.

In a further embodiment there is provided a kit when used in a method of the invention mentioned above, the kit including:
   a container holding dexpanthenol or pharmaceutical composition or contact lens care solution of the invention; and
   a label or package insert with instructions for use.

In certain embodiments the kit may contain one or more further ingredients for the prevention and/or treatment of one or more of contact lens papillary conjunctivitis, mechanical trauma and friction-induced eye disease and allergic eye disease, preferably contact lens papillary conjunctivitis.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

As discussed above, it has been found that when dexpanthenol is included in pharmaceutical compositions it reduces the occurrence of papillae on the upper tarsal conjunctiva and also reduces signs of redness of the eye. Dexpanthenol also has the advantage of reducing side effects commonly associated with the use of long term therapy with non-steroidal anti-inflammatory agents and corticosteroids, which are commonly used in the treatment of allergic eye disease.

It has also been found that in a group of contact lens wearers using different types of contact lenses on a daily wear basis, the use of a contact lens care composition containing dexpanthenol compared to the use of a composition without dexpanthenol in a contact lens wearing group resulted in no events of contact lens papillary conjunctivitis in the group using the preparation.

A person skilled in the art will be aware that eye conditions such as epithelial lesions, dry eye and Sicca syndrome are conditions that affect the cornea. In contrast, the conditions treated and/or prevented in accordance with the present invention (i.e. contact lens papillary conjunctivitis and allergic eye disease) relate to an inflammation of the upper tarsal conjunctiva (ie the inside of the eyelid). These conditions are also associated in contact lens wearers. Similarly, non-allergic conjunctivitis (i.e. pink eye) is a condition that affects the white of the eye and accordingly, is a different condition to the type of condition contemplated by the present invention.

In addition, "mechanical trauma" and "friction-induced eye disease" refer to conditions affecting the inner eyelid and/or tarsal conjunctiva caused by foreign bodies (e.g. sand and grit), microbial or chemical insult, particularly during contact lens wear. Wearing contact lens can also lead to these conditions.

Dexpanthenol (also referred to as D-panthenol, bepanthen or panthenol) is the alcohol analog of the dextrorotatory isomer of pantothenic acid (vitamin $B_5$) and belongs to the group of water-soluble vitamins.

The terms "treating" or "treatment" refer to administering to a subject a therapeutically effective amount of a composition containing dexpanthenol, such that the subject has an improvement in the condition to be treated (e.g. allergic eye disease or contact lens papillary conjunctivitis). It will be recognised that the treatment may improve the condition, but may not provide a complete cure for the condition.

The terms "preventing" or "prevention" refer to administering to a subject a therapeutically effective amount of a composition containing dexpanthenol, such that the signs and/or symptoms of a condition (e.g. allergic eye disease, preferably contact lens papillary conjunctivitis) are averted, delayed or reduced in frequency in the subject, relative to a subject who does not receive the composition. Prevention does not require that the condition or symptoms are permanently avoided. In addition, the term "prevention" is used in its clinical sense to mean inhibit a disease occurring, rather than in an absolute sense of making it impossible for the disease to ever occur in a given subject. Hence, inhibition of progression to disease or reduced new disease amounts to "prevention" within the meaning of this specification, even if there is pre-existing disease.

The terms "therapeutically effective amount" or "effective amount" refer to an amount of dexpanthenol that results in an improvement or remediation of the symptoms of the disease or condition.

The term "pharmaceutical composition" refers to a composition comprising dexpanthenol, which is dispersed in a pharmaceutically acceptable carrier. The composition may further include one or more additional excipients, such as diluents, emulsifiers, buffers, stabilizing agents, binders, fillers, and the like.

The term "active" refers to a material that has interaction with or effect on any cell or tissue in an animal body (e.g. a human body).

The term "ophthalmic device" refers to an object that resides in or on the eye. The device may provide optical correction or may be cosmetic. Ophthalmic devices include but are not limited to soft contact lenses, intraocular lenses, overlay lenses, ocular inserts, punctual plugs, and optical inserts. The preferred ophthalmic devices of the invention are contact lenses, in particular soft contact lenses, made from silicone elastomers or hydrogels, which include but are not limited to silicone hydrogels, and fluorohydrogels. The ophthalmic devices may be "single-use" devices e.g. single-use or daily contact lenses.

The term "administering" or "administration" means placing the dexpanthenol composition or ophthalmic device containing dexpanthenol onto the surface of the eye, or in the eye, of a subject. Typically such a device (e.g. a soft contact lens) is in contact with the anterior surface of the subject's eye for 8 to 16 hours daily. Alternatively, the dexpanthenol may be placed into or onto an ocular insert as a method of drug delivery. Typically such an ocular insert is inserted into the space between the lids and the sclera (fornix) and gradually releases the drug. Alternatively, a biodegradable collagen lens soaked in dexpanthenol may be placed onto the surface of the eye, or inserted into the eye, of a subject. Typically the collagen lens slowly dissolves and improves patient symptoms.

The subject is a human subject that will usually be a contact lens wearer or a subject that is a suitable candidate for wearing contact lenses.

As used herein, except where the context requires otherwise, the term "comprise" and variations of the term, such as "comprising", "comprises" and "comprised", are not intended to exclude further additives, components, integers or steps.

The pharmaceutical composition of the present invention may be an ophthalmic composition, which is a composition suitable for administration to the eye. Examples of ophthalmic compositions according to the invention are suspensions, ointments, gels, sprays, sustained release formulations or solutions suitable for application as an eye drop. The composition may be applied directly to a contact lens or otherwise be a contact lens care solution in which the contact lens is soaked, prior to being fitted to the subject's eye. Without being bound by any particular mode of action, it is believed that that this would allow for the active that may be absorbed onto the matrix of the contact lens or coated onto the surface of the contact lens, then slowly released into or onto the treatment area, particularly the eyelid and/or upper tarsal conjunctiva, once fitted to the eye.

Aqueous solutions (including those released from soft contact lenses) are generally preferred, based on ease of formulation, as well as a subject's ability to easily administer such compositions by means of instilling one to two drops of the solution in the affected eyes. In the case of contact lenses, the administration of the solution is simplified in that the contact lens and the solution are applied in the one step. However, the compositions may also be suspensions, viscous or semi-viscous gels, or other types of solid or semi-solid compositions, or those appropriate for sustained release.

In the case of a spray, the composition may be applied to the inside of the eyelid (the patient turning their eyelid inside-out to allow application of the spray). The pharmaceutical composition of the present invention may also be applied as a solution whereby soft contact lenses, including silicone hydrogel lenses, may absorb the solution or coat the surface, and then release it when fitted on the eye. The last option has an advantage in that the contact lens maintains the solution in contact with the eye-lid every time the wearer blinks, as opposed to eye drops or a spray which may be relatively quickly drained off the eye by the normal tear action.

Any of a variety of carriers may be used in the compositions of the present invention including water, mixtures of water and water-miscible solvents, such as $C_1$- to $C_7$-alkanols, vegetable oils or mineral oils comprising from 0.5 to 5% non-toxic water-soluble polymers, gelling products, such as gelatin, alginates, pectins, tragacanth, karaya gum, xanthan gum, carrageenan, agar and acacia, and their derivatives, starch derivatives, such as starch acetate and hydroxypropyl starch, cellulose and its derivatives and also other synthetic products, such as polyvinyl alcohol, polyvinylpyrrolidone, polyvinyl methyl ether, polyethylene oxide, preferably cross-linked polyacrylic acid, such as neutral Carbopol, or mixtures of those polymers, naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

The composition according to the present invention may comprise at least one gelling agent. Gelling agents suitable for use in pharmaceutical compositions are well known to those of ordinary skill in the art and include, for example, xanthan gum and its derivatives, carbomer and its derivatives, acrylate based copolymers and cross polymers, sodium polyacrylate and its derivatives, cellulose and its derivatives, and starch and agar and their derivatives.

The selection of the gelling agent according to the present invention is important in providing a clear gel.

The amount of gelling agent added to the composition may be readily determined by one of ordinary skill in the art with a minimum of experimentation, and will depend upon factors known to those skilled in the art, such as the properties of the gelling agent and the desired properties of the pharmaceutical composition.

Additional ingredients that may be included in the pharmaceutical composition of the invention include tonicity enhancers, preservatives, stabilizers, non-toxic excipients, demulcents, sequestering agents, pH adjusting agents, co-solvents and viscosity building agents.

For the adjustment of the pH, preferably to a physiological pH, buffers may especially be useful. The pH of the present solutions should be maintained within the range of between 6.5 to 8.0, preferably 7.2 to 7.5. It will be understood by a person of ordinary skill in the art that any pH that is compatible with the ocular surface is suitable. Suitable buffers may be added, such as boric acid, sodium borate, potassium citrate, citric acid, sodium bicarbonate, TRIS, disodium edetate (EDTA) and various phosphate buffers (including combinations of NaCl, KCl, $Na_2HPO_4$, $NaH_2PO_4$ and $KH_2PO_4$) and mixtures thereof. In one embodiment, the buffer used contains concentrations of about NaCl 8 g/L, KCl 0.2 g/L, $Na_2HPO_4$ 1.15 g/L and $KH_2PO_4$ 0.2 g/L.

Tonicity is adjusted if needed typically by tonicity enhancing agents. Such agents may, for example, be of ionic and/or non-ionic type. Examples of ionic tonicity enhancers are alkali metal or earth metal halides, such as, for example, $CaCl_2$, KBr, KCl, LiCl, NaI, NaBr or NaCl, $Na_2SO_4$ or boric acid. Non-ionic tonicity enhancing agents are, for example, urea, glycerol, sorbitol, mannitol, propylene glycol, or dextrose. The aqueous solutions of the present invention are typically adjusted with tonicity agents to approximate the osmotic pressure of normal lachrymal fluids.

In certain embodiments, the compositions of the invention additionally comprise a preservative. A preservative may typically be selected from a quaternary ammonium compound such as benzalkonium chloride (N-benzyl-N—($C_8$-$C_{18}$-alkyl)-N,N-trimethylammonium chloride), benzoxonium chloride or the like. Examples of preservatives different from quaternary ammonium salts are alkyl-mercury salts of thiosalicylic acid, such as, for example, thiomersal, phenylmercuric nitrate, phenylmercuric acetate or phenylmercuric borate, sodium perborate, sodium chlorite, parabens, such as, for example, methylparaben or propylparaben, sodium benzoate, salicylic acid, alcohols, such as, for example, chlorobutanol, benzyl alcohol or phenyl ethanol, guanidine derivatives, such as, for example, chlorohexidine or polyhexamethylene biguanide, sodium perborate, Germal®π or sorbic acid. Preferred preservatives are quaternary ammonium compounds, in particular benzalkonium chloride or its derivative such as Polyquad (see U.S. Pat. No. 4,407,791), alkyl-mercury salts and parabens. Other suitable preservatives include polymyxin B sulphate and Purite®. Where appropriate, a sufficient amount of preservative is added to the ophthalmic composition to ensure protection against secondary contamination during use caused by bacteria and fungi.

In other embodiments, the compositions of this invention do not include a preservative, ie are preservative free. Such formulations would be particularly useful for subjects who wear contact lenses.

The compositions may comprise further non-toxic excipients, such as, for example, emulsifiers, wetting agents or fillers, such as, for example, the polyethylene glycols designated 200, 300, 400 and 600, or Carbowax designated 1000, 1500, 4000, 6000 and 10000. The amount and type of excipient added is in accordance with the particular requirements.

Other compounds may also be added to the compositions of the present invention to increase the viscosity of the carrier. Examples of viscosity enhancing agents include, but are not limited to: polysaccharides, chondroitin sulfate and its salts, dextrans, various polymers of the cellulose family; vinyl polymers; and acrylic acid polymers.

The composition may be administered in any way that is deemed suitable by a person of ordinary skill in the art. The pharmaceutical composition may be administered topically. The composition of the invention may be administered in single or multiple doses and for any length of time until the disease is either completely treated or until the desired level of treatment has been achieved. The person of ordinary skill in the art will recognise that the dosage amount, dosage regime and length of treatment will depend on factors such as, for example, the disease type, the location of the disease and the health of the subject. In the case of a contact lens care solution, the composition may be administered once a day (when the contact lens is applied). Alternatively, the contact lens may be stored in the care solution (eg overnight) whilst not being worn by the subject. In the case of eye drops, the composition may be administered every half hour or hourly, up to, for example, eight times a day.

The ophthalmic device containing dexpanthenol may be prepared by contacting a solution containing dexpanthenol with the ophthalmic device. Dexpanthenol may be contacted with the ophthalmic device prior to selling or delivering the ophthalmic device to a subject (e.g. adding dexpanthenol to a solution prior to sealing the package, and subsequently sterilizing the package) or during the preparation of the ophthalmic device. As outlined above, in one embodiment, dexpanthenol is incorporated into liposomes which are attached to the device (such as a lens) and which then permit the dexpanthenol to be released during wearing of the device.

Sterilization can take place at different temperatures and periods of time. Sterilization is preferably carried out using filter sterilization.

The "solutions" that are used in methods of this invention are typically water-based (i.e. aqueous) solutions. Typical solutions include saline solutions, other buffered solutions, and deionized water. The preferred aqueous solution is deionized water or saline solution containing salts including sodium chloride, sodium borate, sodium phosphate, sodium hydrogen phosphate, sodium dihydrogenphosphate, or the corresponding potassium salts of the same. These ingredients are generally combined to form buffered solutions that include an acid and its conjugate base, so that addition of acids and bases cause only a relatively small change in pH. The buffered solutions may additionally include 2-(N-morpholino)ethanesulfonic acid (MES), sodium hydroxide, 2,2-bis(hydroxymethyl)-2,2',2"-nitrilotriethanol, n-tris(hydroxymethyl)methyl-2-aminoethanesulfonic acid, citric acid, sodium citrate, sodium carbonate, sodium bicarbonate, acetic acid, sodium acetate, ethylenediamine tetraacetic acid and the like and combinations thereof. Preferably, the solution is a borate buffered or phosphate buffered saline solution or deionized water. The particularly preferred solution contains about NaCl 8 g/L, KCl 0.2 g/L, $Na_2HPO_4$ 1.15 g/L and $KH_2PO_4$ 0.2 g/L buffer.

The kit or "article of manufacture" may comprise a container and a label or package insert on or associated with the container. Suitable containers include, for example, bottles, vials, syringes, blister pack, etc. The containers may be formed from a variety of materials such as glass or plastic. The container holds dexpanthenol or a pharmaceutical composition which is effective for treating the condition and may have a sterile access port (for example the container may be an intravenous solution bag or a vial having a stopper pierceable by a hypodermic injection needle). The label or package insert indicates that dexpanthenol or the pharmaceutical composition is used for treating the condition of choice. In one embodiment, the label or package insert includes instructions for use and indicates that the therapeutic composition can be used to prevent and/or treat allergic eye disease, preferably contact lens papillary conjunctivitis.

The kit may comprise (a) dexpanthenol or a pharmaceutical composition or contact lens care solution as described above; and (b) a second container comprising a solution that is suitable for application to the eye, carriers, excipients, and the like. The kit in this embodiment of the invention may further comprise one or more package inserts. The inserts, for example, indicate how dexpanthenol or the pharmaceutical composition and the excipient can be used to prevent and/or treat contact lens papillary conjunctivitis or other eye disease, and provide instructions for use of the kit. The second container may comprise a solution that is suitable for application to the eye (e.g. an aqueous solution) and/or pharmaceutically-acceptable buffers, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may also comprise (a) dexpanthenol or a pharmaceutical composition or contact lens care solution; and (b) a contact lens. The kit in this embodiment of the invention may further comprise one or more package inserts. The inserts may, for example, indicate that dexpanthenol or the pharmaceutical composition and the contact lens can be used to prevent and/or treat allergic eye disease, preferably contact lens papillary conjunctivitis, and provide instructions for use of the kit.

It will be understood that the invention disclosed and defined in this specification extends to all alternative combinations of two or more of the individual features mentioned or evident from the text or drawings. All of these different combinations constitute various alternative aspects of the invention.

EXAMPLES

The present invention will now be more fully described with reference to the accompanying examples and drawings. It should be understood, however, that the description following is illustrative only and should not be taken in any way as a restriction on the generality of the invention described above.

The following tables provide two examples of compositions of the invention. The compositions both contain dexpanthenol, buffer (NaOH/HCl) and a tonicity agent (sodium chloride), and Composition 1 contains a preservative (benzalkonium chloride or alkyldimethylbenzylammonium chloride), while Composition 2 is preservative-free.

Composition 1

Topical Drops

| Ingredient | Concentration (wt %) |
|---|---|
| Dexpanthenol | 2% |
| Sodium Chloride | 0.65% |
| Benzalkonium Chloride | 0.01% |
| NaOH/HCl | pH 6-8 |
| Purified Water | q.s* 100 |

Composition 2

Unit Dose Preservative-Free Preparation

| Ingredient | Concentration (wt %) |
|---|---|
| Dexpanthenol | 2% |
| Sodium Chloride | 0.65% |
| NaOH/HCl | pH 6-8 |
| Purified Water | q.s* 100 |

*quantity sufficient

To demonstrate the effect of the dexpanthenol, a study was conducted of about 800 patients. The patients wore different types of contact lenses on a daily wear basis for a period of three months, which had been soaked overnight in either a contact lens care solution without dexpanthenol (the control group) or a care solution that contains dexpanthenol (such as Composition 1 or Composition 2). The comfort of the lens wear was assessed subjectively by each patient, and the incidence of contact lens papillary conjunctivitis or other eye disease was assessed by an optometrist.

It was found that, after a three month period, in the group using a composition with dexpanthenol, no incidences of contact lens papillary conjunctivitis occurred, compared to the control group (0% in eyes using contact lens care formulation with dexpanthenol (n=239) compared with 1.1% in eyes using contact lens care formulation without dexpanthenol (n=559)). This indicates that the composition treated any existing disease and inhibited new disease.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method for the treatment of the symptoms of contact lens papillary conjunctivitis in a subject, comprising:
administering directly to the eye of the subject a therapeutically effective amount of a pharmaceutical composition, wherein panthenol, dexpanthenol, or a combination of both compounds is the only active ingredient in the pharmaceutical composition.

2. The method of claim 1, wherein the pharmaceutical composition comprises 0.001 to 10% by dry weight panthenol, dexpanthenol, or combination of both compounds.

3. The method of claim 2, wherein the panthenol, dexpanthenol, or combination of both compounds is present in an amount of 0.01 to 5% by dry weight.

4. The method of claim 3, wherein the panthenol, dexpanthenol, or combination of both compounds is present in an amount of about 2% by dry weight.

5. The method of claim 1, wherein the pharmaceutical composition comprises an eye drop.

6. The method of claim 1, wherein the pharmaceutical composition is in the form of an ophthalmic composition selected from the group consisting of a suspension, ointment, gel, spray, and sustained release formulation.

7. The method of claim 6, wherein the spray is applied directly to the inside of the eyelid.

8. The method of claim 1, wherein the pharmaceutical composition is in the form of a viscous gel, semi-viscous gel, solid, or semi-solid.

9. The method of claim 1, wherein the pharmaceutical composition comprises one or more carriers.

10. The method of claim 9, wherein the one or more carriers are selected from the group consisting of water, mixtures of water and water-miscible solvents, vegetable oils, and mineral oils.

11. The method of claim 1, wherein the pharmaceutical composition comprises an aqueous solution.

12. The method of claim 1, wherein the pharmaceutical composition is in the form of one or more dispersible powders or granules suitable for preparation of an aqueous solution.

13. The method of claim 1, wherein the pharmaceutical composition is in the form of an admixture with a dispersing, suspending, or wetting agent.

14. The method of claim 1, wherein the pharmaceutical composition comprises at least one gelling agent.

15. The method of claim 14, wherein the gelling agent provides a clear gel.

16. The method of claim 1, wherein the pharmaceutical composition comprises one or more tonicity enhancing agents.

17. The method of claim 1, wherein the pharmaceutical composition comprises one or more preservatives.

18. The method of claim 1, wherein the pharmaceutical composition comprises one or more stabilizers.

19. The method of claim 1, wherein the pharmaceutical composition comprises one or more excipients.

20. The method of claim 1, wherein the pharmaceutical composition comprises one or more demulcents.

21. The method of claim 1, wherein the pharmaceutical composition comprises one or more sequestering agents.

22. The method of claim 1, wherein the pharmaceutical composition comprises one or more pH adjusting agents.

23. The method of claim 22, wherein the pH adjusting agent comprises one or more buffers.

24. The method of claim 1, wherein the pharmaceutical composition comprises one or more cosolvents.

25. The method of claim 1, wherein the pharmaceutical composition comprises one or more viscosity building agents.

26. The method of claim 1, wherein the pharmaceutical composition is administered topically.

27. The method of claim 1, wherein the pharmaceutical composition is administered in a single dose.

28. The method of claim 1, wherein the pharmaceutical composition is administered once daily.

29. The method of claim 1, wherein the pharmaceutical composition is administered in multiple doses.

30. The method of claim 1, wherein the pharmaceutical composition is administered more than once daily.

31. The method of claim 1, wherein the pharmaceutical composition is administered until a desired level of treatment has been achieved.

* * * * *